United States Patent
Wurzburger et al.

(10) Patent No.: US 6,331,514 B1
(45) Date of Patent: Dec. 18, 2001

(54) STERILIZING AND DISINFECTING COMPOUND

(76) Inventors: Stephen R. Wurzburger, P.O. Box C, Goodyear Bar, CA (US) 95944; James Michael Overton, 1127 Nickel La., Yuba City, CA (US) 95911

( * ) Notice: Subject to any disclaimer, the term of this patent is extended or adjusted under 35 U.S.C. 154(b) by 0 days.

(21) Appl. No.: 09/307,100

(22) Filed: May 7, 1999

Related U.S. Application Data

(63) Continuation-in-part of application No. 08/994,547, filed on Dec. 19, 1997, now abandoned, which is a continuation-in-part of application No. 08/911,773, filed on Aug. 15, 1997, now Pat. No. 5,895,782, which is a continuation-in-part of application No. 08/701,776, filed on Aug. 26, 1996, now Pat. No. 5,830,838.

(51) Int. Cl.$^7$ ............................... C11D 7/08; C11D 7/10; B08B 3/04; B08B 3/08
(52) U.S. Cl. ........................ 510/254; 510/272; 510/405; 510/418; 134/3; 134/41; 134/42
(58) Field of Search ..................... 514/772.3; 510/254, 510/272, 405, 418; 134/3, 41, 42

(56) References Cited

U.S. PATENT DOCUMENTS

| | | | |
|---|---|---|---|
| 3,125,521 | 3/1964 | Wentworth | 167/13 |
| 3,585,147 | 6/1971 | Gordon | 252/187 |
| 3,991,515 | 11/1976 | Lovely | 252/187 |
| 5,650,446 | * 7/1997 | Wellinghoff et al. | 514/772.3 |

* cited by examiner

Primary Examiner—Theodore J. Criares

(57) ABSTRACT

A method and application of a disinfecting solution which comprises adding to an acid the chemical equivalent of a metal chloride plus a metal compound wherein the metal compound is one of a hydride, oxide or hydroxide and the metal is selected to form a precipitate with said acid. The precipitate is filtered from the solution leaving a deanionated chlorided hydronium complex that is non corrosive to human tissue yet has powerful disinfecting properties. Calcium is the preferred metal.

5 Claims, 3 Drawing Sheets

STERILIZING AND DISINFECTING COMPOUND

CROSS REFERENCE TO EARLIER FILED APPLICATIONS

This application is a continuation-in-part of application Ser. No. 08/994,547 filed Dec. 19, 1997, now abandoned which is a continuation-in-part of application Ser. No. 08/911,773, filed Aug. 15, 1997 now U.S. Pat. No. 5,895,782, which is a continuation-in-part of application Ser. No. 08/701,776 filed Aug. 26, 1996 now issued as U.S. Pat. No. 5,830,838 from all of which priority is claimed.

FIELD OF THE INVENTION

This invention relates to a composition useful for sterilizing and disinfecting E. coli and salmonella infected foods, materials and surfaces and particularly to a compound having a higher concentration of hydronium ion.

PRIOR ART AND INFORMATION DISCLOSURE

In the past few years there has been a marked increase in the number of E. coli or other food born pathogen outbreaks. While some of these can be traced back to contaminated foods (food spoilage), other cannot. It must therefore be assumed that most of these outbreaks are caused by secondary contamination sources such as from the facilities used to prepare the food or from the preparers. In view of these outbreaks, concern has intensified in developing and practicing improved techniques of food preparation.

Many types of disinfecting and sterilizing agents have been investigated with limited success.

The term "sterilization" generally infers that the sterilizing agent has eliminated all viable microorganisms found on food or in food preparation areas. This also includes spores of the microorganisms. In contrast, the term "disinfection" generally refers to the process of killing microorganism or sometimes merely reducing the potential infectivity of the material and does not necessarily imply removal or destruction of all the living microorganisms and their spores. At this time, the most commonly used household or commercial methods of disinfection or sterilization employ heat or chemical agents. The most common instance of application of heat is in boiling water. Under ideal conditions at sea level, the best kill expressed logarithmically is log 4 (99.99%) The boiling temperature must be maintained for 20 minutes or more.

It is generally believed that the use of boiling water results in sterilized water. In fact, the water may only be disinfected and not sterilized. In fact, boiling will not kill or even inactivate all of the spores of such microorganisms and they remain viable at 212° F. (boiling point at sea level). Above 5000 feet, boiling occurs below 200° F. and does not kill the most dangerous pathogens and microorganisms. With a change in environment, these inactivated pathogens can be revived or spores can again be activated into active organisms which, even if present in small numbers, can reproduce to large numbers in a short period of time.

The most commonly used disinfection or sterilizing agent is dissolved chlorine gas, which is generated by these agents.

There are many many methods which rely on other chemical agents but these methods are characterized by a number of disadvantages.

One such method requires the use of sodium hypochlolite and other chlorine gas generating chemicals. These solutions result in release of free chlorine gas into water which, in most situations, can cause a problem.

Chlorine gas is objectionable since in aqueous solution, it forms hypochlorous acid and has a very sharp odor in concentrations as low as 3.5 parts per million. It forms toxic and possibly carcinogenic organic halogen compounds while causing irritation of the pulmonary mucosa.

A number of halogen containing compounds, such as, for example, chlorine dioxide, bromine oxide, bromine chloride, monochloroamine, bromic acid, hypochlorous acid, chlorates, hypochlorites, iodine monochloride, iodine trichloride and iodine monobromide, among others are known to be effective disinfectants and sterilizing agents if applied in proper concentrations. In particular, chlorine dioxide has been used for many years to treat municipal water supplies and has recently been demonstrate to be effective as a medical and dental equipment sterilizer, as a disinfectant and deodorizer for beds, as fungicide, as toothpaste additive used to prevent dental cavities and as a mouthwash additive.

Chlorine dioxide has been demonstrated to result in the destruction of many microorganisms and their spores at strengths as low as 0.75 ppm; as little as 1 ppm of chlorine dioxide in solution will kill or inactivate 99.99% of Escherichia coli bacteria upon contact for five minutes. Chlorine dioxide has also been effective in inactivating, among others, bacteria such as Bacillus anth acoides, B subtilis, B. cereus, B. stearothermilus, B. mesentericus, B. megatherium, Clostridium pergigens, Erberthella typhose, Pseudomonosa aeruginosa and viruses such as HTL-III, polio-virus, Sendaivirus, Vaccina virus, Bacteliophae f2, Coliphage and phage ØX 174.

However, some of such halogen containing compounds such as chlorine dioxide, bromine oxide, bromine chloride and monochloroamine among others are unstable and there have been a number of problems associated with such instability. In particular, the use of chlorine dioxide is somewhat problematic because, at 25° C., it exists as a yellow gas which is explosive and may detonate under certain conditions. Thus chlorine, being readily soluble in water, is usually stored as an aqueous solution at a low temperature to reduce its instability. Such halogen containing compounds, (e,g. chlorine dioxide, bromine oxide, monochloroamine and bromine chloride and, in particular, chlorine dioxide), even though in solution, remain unstable in the sense that they have relatively high rates of chemical breakdown or dissociation, particularly in light. These high rates of chemical breakthrough or dissociation render them inefficient and sometimes totally in effective.

In order to reduce the dissociation of such compounds in solution and take advantage of their excellent sterilization properties, there have been attempts either to provide stable stable solutions of such compounds or to generate such compounds at their place and time of use. For industrial or commercial applications having the necessary equipment and other resources, the chlorine dioxide is generally produced and used immediately. With household or other non-industrial; applications, it is not cost effective, feasible or safe to do this. There have thus been attempts to provide stable chlorine dioxide solutions such as disclosed in U.S. Pat. Nos. 3,112,352 and 3,585,147 and 3,591,515 among others. In most of these situation, the chlorine dioxide is provided by releasing the gas by acidification of solutions in which the chlorine dioxide is made more stable by the addition of a peroxide or boron compounds. While this results in an increase of effective shelf life, of such chlorine dioxide generating solutions, there is still significant spontaneous breakdown of the chlorine dioxide and consequently the sterilizing capacity of the solution is rapidly diminished.

Preparation and of chlorine dioxide gas and purification to remove free chlorine is disclosed in Kirk-Othmer, Encyclopedia of Chemical Technology, vol. 5. pages 615–617 and Chlorine Dioxide: Chemistry and Environmental Impact of Oxychlorine Compounds by W. S. Masschelin, Ann Arbor Science publishers, Inc. (1979 pages 9–11 and 112–140, the relevant portions of which are incorporated by reference.

In view of problems such as noted above, satisfactory methods of storing and/or transpiring such halogen containing compounds which allow them to retain their disinfecting properties have not been readily available. The result has been that it has not always been possible to utilize to its full potential the excellent disinfectant and sterilizing capability of chlorine dioxide and such other unstable halogen containing compounds. particularly in household and other non-industrial applications.

It is also known that strong acids and alkalies have great potential as sterilizing and disinfecting agents. These agents, in the strengths necessary to be an effective sterilizing or disinfecting agent are corrosive to flesh so there use is limited. It should be noted that a concentrated solution of hydronium ions will not only kill most microorganisms. It also dissolves the organisms and has the ability to destroy (dissolve) the toxins in the microbes as well as most spores.

The use chlorine dioxide, while being the most widely used disinfectant is essentially the "best of all evils". A difficult problem has been that, due to the volatility of the gas, in use such as in water supplies, its concentration diminishes over time so that more than enough is added initially in order to maintain a sufficient concentration over a period of time. The problem is that the inescapably harmful effects are accentuated, particularly when the first additions are made, such as to a water supply.

These effects are not only the attacks of the chemical on the human—we are all familiar with the burning of the eyes after bathing in a community pool where specially high concentrations of the chloride dioxide is added,—but it is also found that the heavy chlorinated water can cause pitting of the stainless steel fittings that are used in food processing.

Conventional technologies say that biofilms can be controlled by use of microbiocides, biodispersants, and by limiting nutrient. Microbiocides, both oxidizing and non-oxidizing can be effective in overall biofilm control when applied properly. The oxidizing microbiocides, such as chlorine dioxide and ozone can be extremely effective in destroying both the extracellular polysaccharide and the bacterial cells. When using oxidizing microbiocides, one must be sure to obtain a sufficient residual for a long enough duration to effectively oxidize the biofilm. Unfortunately, there are those who are overly concerned with the corrosive nature of the oxidizing microbiocides and fail to apply the needed residual oxidant required to control biofilm. Low residual levels may significantly reduce planktonic counts but may not be sufficient to control biofilm. The level of oxidant and duration required will vary from system to system. It is generally more effective to maintain a high residual for several hours than it is to continuously maintain a low residual.

Extended use of these materials causes degradation of the interior of the stainless steel piping (corrosion and pitting which is regularly sloughed off with pieces of the biofilm infecting any product being manufactured, An effective biofilm treatment must not only remove the biofilm but be able to kill any bacteria within the film without being corrosive to the stainless steel pipe.

An apparatus (MicroWater™ distributed by Optimum Health Institute, San Mateo, Calif.) has been disclosed. The device produces two kinds of water with different redox potentials, one with a high reduction potential (referred to as "alkaline MicroWater") and one with a high oxidation potential (referred to as "acid MicroWater").

The acid Microwater has a been found to have commercially viable bactericidal properties when used in the lowest pH range (2.65) attainable (reported) for this solution. It is believed that the active molecule is the "hydronium" ion having the structure:

It would be desirable to produce a solution of substantially exclusively hydronium ions having a pH less than 2.65 that would kill microbes on contact with the solution while not having a deleterious effect on human tissue since such a solution would be expected to have a stronger bactericidal effect than presently available solutions of hydronium ions.

SUMMARY OF THE INVENTION

It is an object of this invention to provide an effective disinfecting agent that is not corrosive to human flesh.

It is another object that the compound be applied as an aqueous solution situations where external incidental contact with human flesh does not lead to any deleterious effects.

It is another object to provide a process for destroying biofilms in systems for preparing food and phamaceuticals.

It is another object to provide an aqueous disinfecting "wash" that can be used to wash produce (fruits and vegetables) without leaving the residues that characterize the use of chemicals presently used for this purpose.

It is another object to present a method for making a solution that has a large concentration of hydronium ions in which anions have been removed by precipitation of an acid with a metal compound selected from the group of compounds that includes metal hydride, metal oxide and metal hydroxide. In accordance with the invention it is an object to provide a disinfecting solution that is stable and has a pH of less than 1.00 and an impurity level that is less than 100 parts per million by weight.

In one embodiment, this invention is directed toward a disinfecting compound and method of use which is made by adding chemical equivalents of a metal and acid together where the metal and acid are selected to create a highly insoluble salt which is then filtered from the solution, leaving an aqueous liquid that is a powerful disinfectant and yet to which organic tissue (human tissue ) and the surfaces of fruits and vegetables is relatively insensitive.

According to one method of practicing the invention, the metal is added as a metal hydride to the strong acid. Specifically, the metal hydride is calcium hydride and is added to a chemically equivalent amount of sulfuric acid resulting in the formation of the highly insoluble calcium sulfate. When filtered to the aqueous solution is left with a concentration of Ca of not more than 2500 ppm and a concentration of sulfate ions of not mere than 2500 ppm and a pH less than 2.5.

In yet another embodiment of the invention, a further reduction of the sulfate ion concentration is achieved by mixing into the solution an alcohol that further reduces the solubility of anions ($SO^{--}$) and cations ($Ca^{++}$) to a level of less than 50 ppm while maintaining a pH of less than 1.00. The alcohol is then distilled from the water.

In another embodiment of the invention, the disinfecting solution is an aqueous solution containing a halogen-hydronium complex which is a highly effective disinfecting agent. According to the invention, the precursor halogen containing compounds used in preparing the disinfectant is selected from a number of compounds including chlorine dioxide, calcium chloride, bromine oxide, bromine chloride, monochloroamine, bromic acid, iodine monochloride, iodine trichloride, and iodine monobromide. Calcium chloride is preferred.

While we do not wish to be bound by theory, it is believed that the solution produced by this invention contains a concentration of hydronium ions in a highly stablized state as indicated by the large reduction potential in the absence of anions that have been removed by precipitation.

DESCRIPTION OF THE BEST MODE

Figure 1:
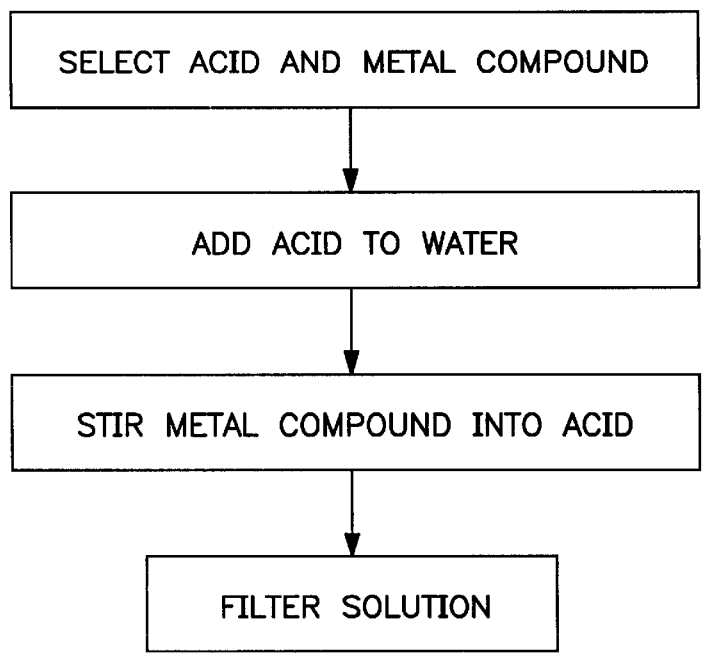
FIG. 1 is a flow diagram of the method for preparing the solution of this invention.

Turning now to a description of the drawings, FIG. 1 is a flow chart listing the steps in generating a solution having a concentration of hydronium ions and in which anions have been removed:

In step 1, an acid is selected and a compound being any one of
  (i) a metal hydride
  (ii) metal hydroxide
  (iii) metal oxide
  (iv) metal; is selected such that the metal cation and acid anion form a virtually insoluble precipitate.

In step 2, a quantity of the acid is added to water;

In step 3, a quantity of the compound is stirred into the acid solution of step 2 wherein the quantity of compound is the gram equivalent of the quantity of acid thereby forming the insoluble salt.

In step 4 solution is filtered to remove the precipitate thereby removing the anion of the acid that has reacted with the metal leaving a "de-anionated" solution containing hydronium ions.

Selection of an appropriate metal and acid can be done by consulting table I which is a table listing the solubilities of salts formed from combining selected metals and acids. In the context of this specification, the term, "insoluble" is defined to mean that less than 0.3 gms of the salt is soluble in 100 gms. of water.

TABLE I

| | sulfuric $H_2SO_4$ | phosphoric $H_3PO_4$ | oxalic HOOCCOOH | stearic $CH_3(CH_2)_{16}COOH$ |
|---|---|---|---|---|
| Calcium | insoluble | insoluble | insoluble | insoluble |
| Magnesium | soluble | insoluble | insoluble | insoluble |
| Barium | insoluble | insoluble | insoluble | insoluble |
| Beryllium | soluble | soluble | soluble | insoluble |

Table I indicates that preparation of the de-anionated hydronium solution of this invention according to FIG. 1 can be performed by selecting as the metal:
  (i) any one of calcium, and Barium and as the acid anyone of sulfuric, phosphoric, oxalic and stearic;
  (ii) magnesium with any acid of phosphoric, oxalic and stearic;
  (iii) beryllium with stearic acid.

As an example of the method of preparation, a solution having a pH of less than 2.5, and less than 2500 parts per million of calcium sulfate is prepared by performing the steps:
  (a) forming a solution of one mole $H_2SO_4$ per one liter of water:
  (b) stirring into said solution of step (a) one Gram Equivalent Weight of $CaH_2$ per one mole of $H_2SO_4$
  (c) filtering the solution of step (b) through an ten micron filter;
  (d) allowing the solution of step (c) to digest for at least 10 hours;
  (e) filtering the solution of step (d) through a two micron filter.

By way of demonstrating the utility of the invention as a disinfecting agent, a sample of the invention was prepared in accordance with the listed steps using triply distilled water. The resultant test sample was found to contain less than 2500 ppm of sulfate and less than 2500 ppm of Calcium. The pH was 2.0. Bactericidal properties of the solution were evaluated by an independent laboratory, BioVir Laboratories, Inc. using the procedure ASTM E 1153-87 which is hereby incorporated as reference into this specification.

The test method was performed in the following manner:
1. 22 mm² coverslips were used for the innocula step (step 3.2).
2. Only 0.6 mL of ARS-I was used on the coverslips.
3. Trypticase Soy Broth (TSB) pH 10 was employed as pH neutralizer.
4. 10 mL of TSB pH 10 with 0.6 mL of the test sample resulted in a final pH 6.7.
5. The test organisms were Staphylcoccous aureus and Enterobacter aerogenes.
6. Sterile petri dishes were substituted for sterile glass jars.

The results of the test are presented in table I.

| Organism/Test | Expected (cfu/mL) | Observed | Log reduction | % reduction |
|---|---|---|---|---|
| S. aureus Control | NA | 50,000 | NA | NA |
| S. aureus A | 50,000 | <1 | >4.5 | 99.995 |
| S. aureus B | 50,000 | <1 | >4.5 | 99.995 |
| S. aureus C | 50,000 | 90 | 2.7 | 99.9 |
| E. aerogenes Ctrl | NA | 53,000 | NA | NA |

| Organism/Test | Expected (cfu/mL) | Observed | Log reduction | % reduction |
|---|---|---|---|---|
| E. aerogenes A | 53,000 | <1 | >4.7 | 99.995 |
| E. Aerogenes B | 53,000 | <1 | >4.7 | 99.995 |
| E. Aerogenes C | 53,000 | <1 | >4.7 | 99.995 |

Conclusion of the testing lab (Bio-Vir):

The conclusion of the third party testing laboratory was that the disinfecting solution of the invention demonstrated a 99.9–>99.99% bactericidal effect within five minutes.

The pH of the test solution resulting from preparing the test solution in accordance with the method of FIG. 1 was measured to be 2.0 compared 2.7 which was the lowest value reported using the electrolysis method discussed in the BACKGROUND of the specification. The lower the attainable pH, it would be expected that the greater would be the bactericidal power of the product. The anion ($SO_4^{--}$) and the cation ($Ca^{++}$) concentration was measured to be less than 2500 ppm.

The reaction of the solution of this invention on human tissue has been tested many times in this laboratory at pH 2.0 and lower and it has been found that there is no reaction whatsoever with periods of fifteen minutes exposure.

While WE DO NOT WISH TO BE BOUND BY THEORY, it is believed that the resultant solution consists essentially of hydionium ions in view of the purity of the water, (being less than 2500 ppm of either Ca or Sulfate) in spite of a pH of 2.0.

We believe that the solution prepared according to the techniques of this invention is an oxidizing acid that can withdraw electrons from bacteria and kill them. The solution contained in sufficient concentration (pH 2.0 or lower) can be used to clean hands and utensils, meat, vegetables, fruit, and sterilize cutting boards and wounds. Tests have shown that solutions of this type can be used effectively to treat athlete's foot, burns, insect bites and wounds. It is excellent for cleansing and household use. It has bleaching ability. It disinfects and sterilizes yet is harmless to the skin. It is an astringent. It tightens skin.

A major advantage of the present invention over the prior art is the ease and economy of preparing the solution. The present method is a chemical method whereas the competing process is an electrophoretic method. The competing process has the major disadvantage that the equipment is relatively expensive and difficult to maintain due to such factors as fouling of filter membranes by metal ions that are initially in the water. Furthermore, the achievable pH of the electrolytic process (reported 2.65) is not as low as can be achieved with the present invention. Another major advantage is that the solution of the present invention maintains a pH of less than 2.5 for longer than 48 hours (actually months compared to the electrolytic process of the prior art where pH remains at 2.65 for only a few hours.

In another embodiment of the invention, a stabilized chlorided hydronium complex solution was prepared as follows:

To make the chlorided hydronium ion complex of this invention, the procedure of FIG. 1 is followed except that mole chemical equivalent of sulfuric acid that is reacted with 1–X mole chemical equivalent of metal compound plus X mole chemical equivalent of calcium chloride where X is the fraction of the chlorided hydronium complex that is chlorine.

Figure 2:
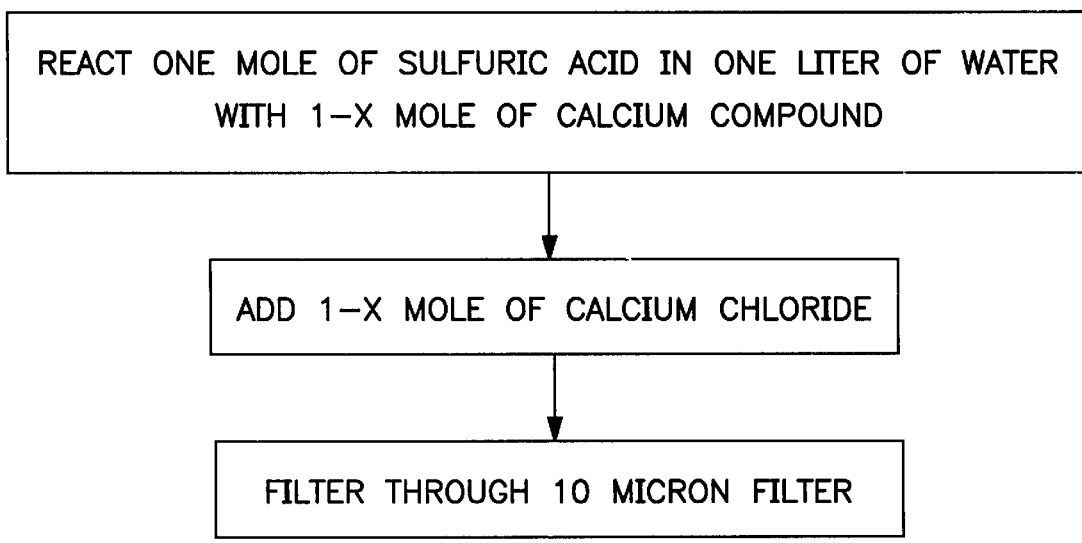
FIG. 2 is a flow chart listing steps in the preparation of the chlorided hydronium complex solution of this invention.

FIG. 2 lists the steps in the preparation of the chlorided hydronium complex.

A. One mole of analytical grade sulfuric acid in one liter of water is reacted with 1–X mole of Calcium hydrate and allowed to digest for several hours. X is a fraction expressing the intended ratio of $Cl^-$ to $H_3O^+$ B. X moles of $Ca\ Cl_2$ is dissolved in one liter of water. The solution of calcium chloride is agitated for fifty minutes.

C. The two solutions are slowly mixed together and the reaction is allowed to go to completion, typically one hour. The solution is then filtered with a 10 micron filter to remove solids.

An effective range for X is from $10^{-4}$ molar to one molar solution depending on the application.

For example, to make a 10% chlorinated solution, 0.1 mole calcium chloride and 0.9 mole of calcium metal or Ca hydrate is used to make the solution.

The solution is slowly mixed together and the reaction is allowed to go to completion i typically one hour. The solution is then filtered with a 10 micron filter.

EXAMPLE I

The following test was performed to test the disinfecting power of a chlorided hydronium complex solution (sample A) made according to the above procedure where X=0.005 giving a solution of pH=0.56

An enrichment culture of *E.Coli* 0157 H 7 was prepared.

An experimental sample was made by placing the culture in a solution of sample A diluted 1:10 at room temperature and incubated for five min.

A control sample was made by placing the culture in a physiologic saline solution at ambient temperature and incubated for five min.

The experimental and control samples were serially diluted and 50 microliters of each dilution were plated in quadruplicate. Culture plates were incubated at 37° C. overnight and the colonies on each plate were enumerated the next morning.

Results

The control sample showed $1 \times 10^9$ colony forming units.

The experimental sample showed 0 colony forming units.

The foregoing test demonstrated that exposure of the *E-Coli* culture to the chlorided hydronium complex reduced the viability of the *E. Coli* 0157H7 by $10^{-9}$ demonstrating that it is an extremely effective disinfectant.

In comparison, the same tests were repeated using standard chlorine containing compounds and kills of $10^{-3}$ were observed demonstrating that the chlorided hydronium disinfecting compound of this invention is one million times more effective than the standard chlorine containing material.

EXAMPLE II

More tests on many kinds of foodstuff which showed dramatically that the chlorided hydronium complex of this invention will kill all water and airborne molds and fungi that destroy food on the grocery shelves.

For example, Several baskets of small tomatoes were purchase. Two baskets of tomatoes were rinsed in tap water and the other two baskets of tomatoes were dipped in the chlorided hydronium complex and allowed to drip dry. A four baskets were left at room temperature. After three days, the untreated tomatoes began to show mold spots. After five days, ⅓ of the untreated tomatoes were very moldy and some had broken down and were putrid. The treated tomatoes had no visible mold or mildew. After seven days, the untreated baskets were totally rotten and the treated tomatoes were still mold and mildew free but there were signs of the tomatoes beginning to deteriorate. These results indicated that the shelf life of fresh fruit and vegetables can be extended by five or six days by washing in the chlorided hydronium complex solution.

EXAMPLE III

In another test, raisins that had about 10% mold contamination were rinsed in chlorided hydronium complex and dried. The treated sample was sent to an EPA field office and retested. The test showed an 80% reduction in the number of mildewed raisins, i.e., less than 2% of the raisins showed mildew.

EXAMPLE IV

Use of chlorinated hydronium complex solution of this invention was also investigated for the removal of biofilms found in the stainless steel pipes in equipment for manufacturing pharmaceuticals and in food processing where protein constituents of the product being processed form a coating on the interior of the pipes that become breeding grounds for pseudomonas aeruginosa and other bacteria. As these coatings become porous, the bacteria infiltrates deeply into the film. As portions of the biofilm flake off, the bacteria within now infects the solution.

As part of the test, sections of stainless pipe from a examined and found to be heavily contaminated with biofilm. After being placed in the chlorided hydronium complex solution heated to 120° F., the pipe sections were visually inspected for plaque and for evidence of corrosion from the complex solution. No plaque was found and no visual corrosion was evident. The samples were cultured and no viable bacteria colonies were observed. Bacteria was killed at a rate greater than >log 6.

Additional tests showed that the stainless steel was not damaged even when very concentrated solutions of the chlorided hydronium complex is applied. Even if the the temperature is raised to 200° F. or treated for several hours, there was no deterioration of the surface of the stainless steel.

In comparison of present standard practice to the methods and compound of this invention, it is noted that sodium hypochlorite and other halogenated chemicals are used that are not totally effective. In some cases, the pipe must be dissembled and mechanically cleaned to remove the coating and then decontaminated with a liquid sterilizing medium after reassembly.

EXAMPLE V

It is well known that viruses of the common cold, influenza and other diseases are spread by human contact with surfaces such as table tops that have collected these viruses by virtue of contact with other humans that are afflicted with these diseases.

A control sample was prepared by applying the physiologic saline solution of EXAMPLE I to an untreated table top, recapturing and incubating a specimen of the exposed control sample overnight.

Then the table top was swabbed with the chlorided hydronium complex solution of EXAMPLE I to which 5 ml per one liter of wetting agent had been added to improve wetability of the table top.

Then, an experimental sample was prepared by applying the physiologic saline solution of EXAMPLE I to the washed table top.

Both the experimental sample and control sample were incubated overnight.

Examination of both samples was conducted and it was observed that substantial colonization had occurred in the control sample and no colonization had occurred in the experimentally.

This test showed that the chlorided hydronium complex is very effective in disinfecting the surfaces that re collecting locations of infectious bacteria.

Many wetting agents are well known in the art. A general class of such compounds are the quaternary amines manufactured by the Shell Co. in Richmond, Calif. Wetting agents are typically mixed with a washing liquid in a concentration of 1 to 10 mgms/liter of solution.

The foregoing examples show the superiority of the solution to disinfecting solutions of the prior art in terms of kill rate combined with minimal deleterious effects. Minimal deleterious effects include benign reaction with human tissue. and in terms of stability resulting in long shelf life.

The method of preparation of the complex provides that the ratio of the chloride to hydronium complex can be selected over a wide range depending on the application and provides that the compound of this invention has application in many areas including treatment of human ailments, preserving food stuffs, sterilizing equipment, etc.

Figure 3:
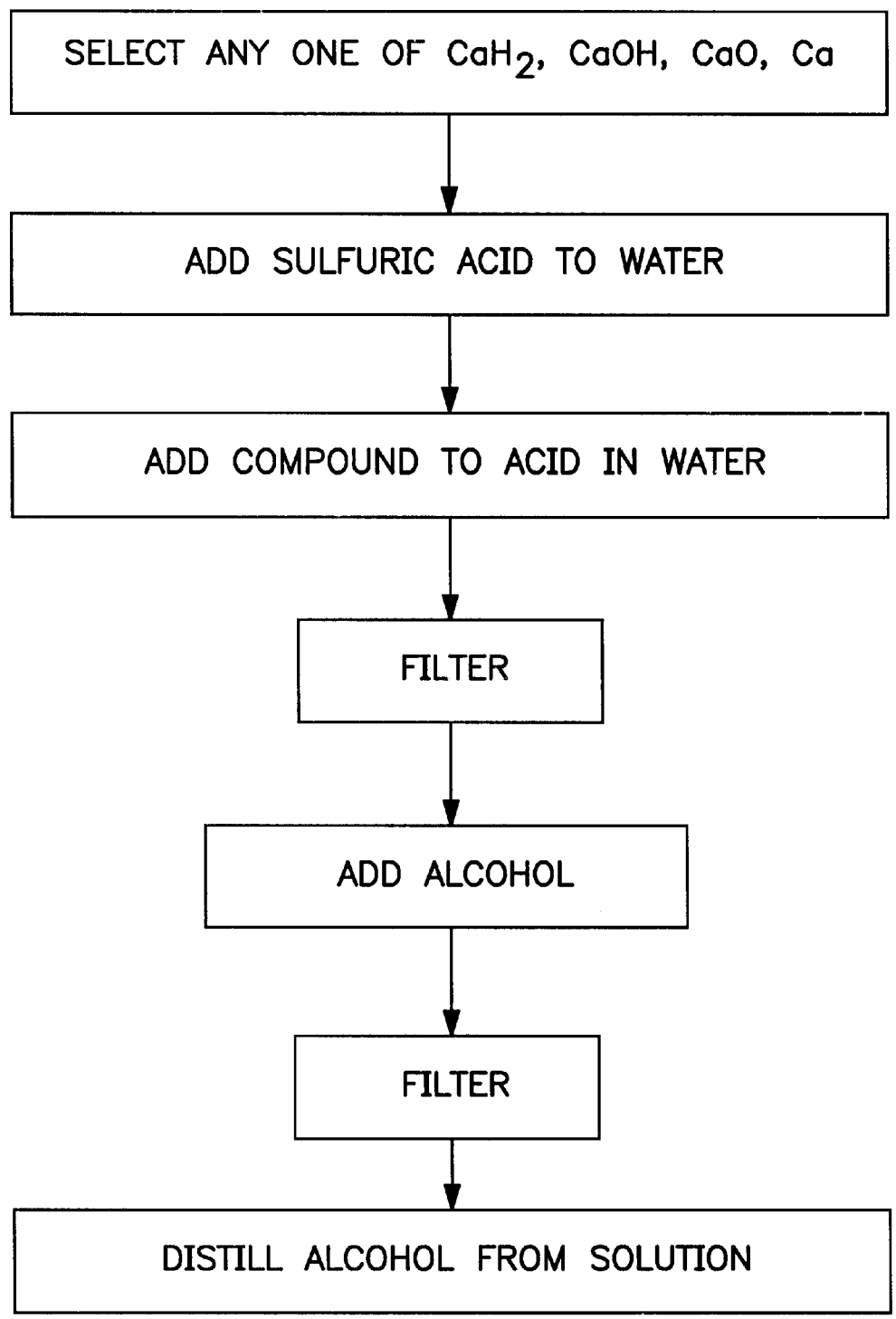
FIG. 3 shows a flow diagram for preparing the solution of this invention and using alcohol to further purify the end solution.
Figure 4:
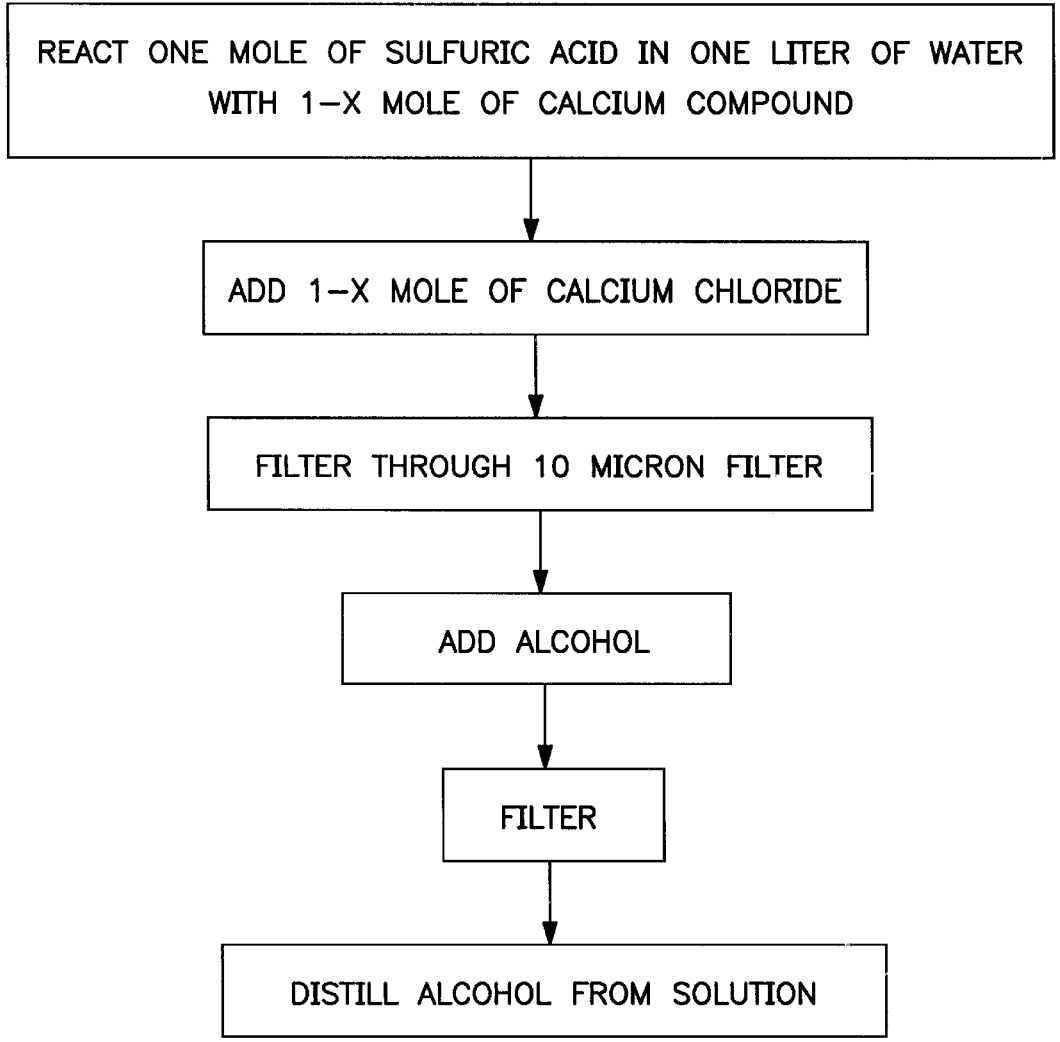
FIG. 4 shows a flow diagram for preparing the chlorided hydronium complex solution of this invention and using alcohol to further purify the end solution.

Another embodiment of the invention is represented in FIG. 3 which is a further refinement of making the solution of the invention resulting in a de-anionated solution of hydronium ions of greater purity than the methods of FIG. 1 and FIG. 2. In step 1, a compound being any one of (i) calcium hydride:
(ii) calcium hydroxide
(iii) calcium oxide or calcium metal is selected, In step 2, a quantity of sulfuric acid is added to water;

In step 3, a quantity of the compound is stirred into the acid solution of step 2 wherein the quantity of sulfuric acid equals the gram molar equivalent of the compound thereby forming a precipitate of calcium sulfate;

In step 4 solution is filtered through a ten micron filter to remove the precipitate.

In step 5 the solution of step 4 is mixed with propyl alcohol according to the ratio 70 parts solution, 30 parts isopropyl alcohol by volume. A cloud of calcium sulfate precipitate is generated from trace amounts calcium and sulfate ions left after step 4.

In step 6 the remaining precipitate generated in step 5 is filtered from solution using a two micron filter.

In step 7, the alcohol is separated from the solution by distillation Using the method of FIG. 3, a de-anionated aqueous solution containing hydronium ions was produced which contained less than 50 parts per million of sulfate ion by volume and in which the pH is less than 0.5. The pH of less than 0.5 is a much more powerful disinfecting agent than the solution of "microwater" produced by electrolysis in which the lowest pH reported is 2.65.

The technique of using alcohol followed by distillation to further remove trace amounts of calcium and sulfate ions may also be applied to produce aqueous chlorided hydronium complex by executing the steps A, B, C listed in FIG. 2 followed by Adding 30% isopropyl alcohol by weight to the solution produced by steps A, B, C; filtering the solution using a two micron filter;

A method has been described for forming an aqueous solution containing hydronium ions by mixing chemical equivalents of a strong acid (sulfuric) with a metal (calcium)

selected to form a a highly insoluble salt (calcium sulfate). The precipitated salt is removed by filtration leaving a "de-anionated" aqueous solution of hydronium ions. The term "de-anionated" should be understood to mean that anions have been extracted from the solution by the precipitation-filtration process. The resulting solution has outstanding properties as a disinfecting agent. This procedure generates a solution that typically has less than 2500 ppm by weight of aqueous solution having a pH of less than 2,5 and is non-corrosive to human tissue.

A method has also been described for producing an aqueous chlorided hydronium complex by applying the technique of the preceding paragraph but supplying a portion of the reacting metal (e.g., calcium) as a chloride.

In both of these procedures, the solution can be further purified (i.e., removal of trace amounts of any remaining cations and anions) by mixing the solution with a suitable hydrogenated hydrocarbon (alcohol, ketone, etc) to precipitate the remaining trace amounts which are then removed by filtration followed by distillation to remove the hydrogenated hydrocarbon leaving a solution of hydronium ions or chlorided hydronium complex having a very low pH (less than 0.5) and high purity (less than 50 ppm by weight of anions)

Variations and modifications may be contemplated after reading the specification and studying the drawings which are within the scope of the invention. For example other halogens are an obvious substitute for chlorine for certain applications in view of the reactions of these elements that are similar to those of chlorine. Any one of a number of hydrogenated hydrocarbons may be used to remove trace remains of elements present in initial stages of the process which are insoluble in the hydrogenated hydrocarbon. The hydrogenated hydrocarbon may include any one of ethanol, methanol, propanol, acetone, methyl ethyl ketone.

In view of these variations, we therefore wish to define the scope of out invention by the appended claims.

We claim:

1. A method for preparing a disinfecting solution which includes the steps:
   (a) selecting one of a group that consists of:
      (i) calcium hydride;
      (ii) calcium hydrate;
      (iii) calcium hydroxide;
      (iv) calcium;
   (b) mixing a quantity of sulfuric acid in water;
   (c) stirring into said sulfuric acid in water a quantity of said one of said group from step (a);
   (d) stirring into said sulfuric acid in water a quantity of calcium chloride;
wherein said quantity of one of group (a) plus said quantity of calcium chloride equals a molar chemical equivalent of said first quantity of said acid;
   (e) passing the solution of step (d) through a 10 micron filter to remove precipitates of salt formed by said metal and said acid and retaining a supernate.

2. The method of claim 1 which further comprises the steps:
   (f) adding 30 parts propyl alcohol to 70 parts of the solution of step (e) by weight;
   (g) removing precipitates from step (f) by passing the solution of step (f) through a filter;
   (h) distilling the solution of step (g) to separate said alcohol from aqueous solution containing hydronium ions whereby said supernate is stabilized.

3. A solution produced by the method of claim 2.

4. A method for preparing a disinfecting solution which includes the steps:
   (a) selecting one of a group that consists of:
      (i) calcium hydride;
      (ii) calcium hydrate;
      (iii) calcium hydroxide;
      (iv) calcium;
   (b) mixing a mole of sulfuric acid in a liter of water,
   (c) stirring into said mole of sulfuric acid in a liter of water a fraction, X, of a mole of said one of said group (a) where X is a value ranging from 0.005 to 0.9;
   (d) stirring into said mole of sulfuric acid in a liter of water another fraction, 1−X, of calcium chloride;
   (e) passing the resultant solution of step (d) through a 10 micron filter to remove precipitates of salt formed by calcium from step (d) and said sulfuric acid.

5. A method for disinfecting stainless steel surfaces which includes the steps:
   providing the solution of claim 2;
   heating said solution to at least 120° F.;
   immersing said stainless steel surface in said solution for a sufficient time to disinfect said surface.

* * * * *